(12) United States Patent
Frederiksen et al.

(10) Patent No.: US 11,517,638 B2
(45) Date of Patent: Dec. 6, 2022

(54) UV LAMP

(71) Applicant: LED iBond International A/S, Hørsholm (DK)

(72) Inventors: Lars Frederiksen, Gentofte (DK); Jesper Breuning-Hansen, Sjællands Odde (DK)

(73) Assignee: LED IBOND INTERNATIONAL A/S, Horsholm (DK)

( * ) Notice: Subject to any disclaimer, the term of this patent is extended or adjusted under 35 U.S.C. 154(b) by 16 days.

(21) Appl. No.: 17/257,368

(22) PCT Filed: Jun. 21, 2019

(86) PCT No.: PCT/EP2019/066552
§ 371 (c)(1),
(2) Date: Dec. 31, 2020

(87) PCT Pub. No.: WO2019/243618
PCT Pub. Date: Dec. 26, 2019

(65) Prior Publication Data
US 2021/0162084 A1  Jun. 3, 2021

(30) Foreign Application Priority Data

Jun. 21, 2018  (DK) .................................. 201870421

(51) Int. Cl.
*A61L 2/10* (2006.01)
*A01J 7/02* (2006.01)
(Continued)

(52) U.S. Cl.
CPC .................. *A61L 2/10* (2013.01); *A01J 7/025* (2013.01); *A61L 2/26* (2013.01); *C02F 1/325* (2013.01);
(Continued)

(58) Field of Classification Search
CPC .......... A61L 2/10; A61L 2/26; A61L 2202/11; A01J 7/025; C02F 1/325;
(Continued)

(56) References Cited

U.S. PATENT DOCUMENTS 4,623,467 A    11/1986  Hamlin
6,276,297 B1 * 8/2001   van den Berg ........... A01J 7/04
                                                        119/14.08
(Continued)

FOREIGN PATENT DOCUMENTS

EP    2481711 A1    8/2012
JP    H1024092 A    1/1998
(Continued)

OTHER PUBLICATIONS

International Search Report issued in corresponding PCT Application No. PCT/EP2019/066552, dated Sep. 13, 2019, pp. 1-3.

*Primary Examiner* — Bao Q Truong
(74) *Attorney, Agent, or Firm* — Robinson & Cole LLP

(57) ABSTRACT

The present invention relates to a UV lamp having an axial dimension normal to a cross-section having a cross-sectional area with a ratio of the axial dimension to the cross-sectional area in the range of 0.1 cm/cm$^2$ to 1000 cm/cm$^2$. The UV lamp includes a first axial conductor separated from a second axial conductor by an electrically insulating material and a light emitting diode (LED) capable of providing light at a wavelength in the range of 100 nm to 400 nm, which LED is mounted to emit light from an outer surface. The invention also relates to a method of sterilising a surface using the UV lamp.

13 Claims, 4 Drawing Sheets

(51) Int. Cl.
*A61L 2/26* (2006.01)
*C02F 1/32* (2006.01)
*F21V 23/06* (2006.01)
*F21V 31/00* (2006.01)
*H01L 33/62* (2010.01)
*F21Y 115/10* (2016.01)

(52) U.S. Cl.
CPC .............. *F21V 23/06* (2013.01); *F21V 31/00* (2013.01); *H01L 33/62* (2013.01); *A61L 2202/11* (2013.01); *C02F 2201/3222* (2013.01); *C02F 2201/3228* (2013.01); *C02F 2303/04* (2013.01); *F21Y 2115/10* (2016.08)

(58) Field of Classification Search
CPC ...... C02F 2201/3222; C02F 2201/3228; C02F 2303/04; F21V 23/06; F21V 31/00; H01L 33/62; F21Y 2115/10
See application file for complete search history.

(56) References Cited

U.S. PATENT DOCUMENTS

| | | | |
|---|---|---|---|
| 2005/0000913 A1* | 1/2005 | Betterly | C02F 1/325 210/748.11 |
| 2012/0248330 A1 | 10/2012 | Lee et al. | |
| 2013/0236353 A1* | 9/2013 | Blechschmidt | C02F 1/325 422/4 |
| 2014/0061706 A1 | 3/2014 | Bae et al. | |
| 2015/0193214 A1 | 7/2015 | Frederiksen | |

FOREIGN PATENT DOCUMENTS

| | | |
|---|---|---|
| WO | 2009022381 A1 | 2/2009 |
| WO | 2009123445 A1 | 10/2009 |
| WO | 2012017000 A1 | 5/2012 |
| WO | 2017121430 A1 | 7/2017 |
| WO | 2017185217 A1 | 11/2017 |

* cited by examiner

UV LAMP

The present invention relates to a UV lamp suited for sterilizing an inner surface of e.g. a teat cup. The UV lamp comprises a first axial conductor separated from a second axial conductor by an electrically insulating material and a light emitting diode (LED) capable of providing UV light.

FIELD

The present invention relates to a UV lamp e.g. for use as a sterilizing lamp for teat cups and to a method of sterilizing a surface using the UV lamp.

BACKGROUND

UV lamps for sterilizing surfaces are widely known in the art. However, none of the known solutions provide UV lamps with a simple and compact design. In particular, sterilizing UV lamps of the prior art are ill-suited for sterilizing difficult to reach sections, such as the interior of a teat cup.

For example, WO 2012/071000 discloses a teatcup liner and a teatcup comprising the teatcup liner. The teatcup liner can have a section that forms a ring module having an inner surface facing the inner space, and the ring module can comprise a functional member providing an additional function to a milking operation, e.g. the functional member may comprise a UV light-emitting element. The UV-light can have a bactericidal effect in order reduce or remove bacteria from the interior of the teatcup liner and thereby from the milk flowing through the teatcup liner.

WO 2017/185217 describes a sterilizing cover with a cover for covering an opening of a container having an inner cavity. The cover serves to prevent bacterial contamination and deterioration from contact with air after sealing, and the cover has a sterilizing illuminating member. The sterilizing cover can be applied to a water bottle, a baby bottle, a medicine bottle, or a cosmetic bottle, where the original cover is replaced with the sterilizing cover which can be closed at the opening of the container so that the inside of the container or the cover body is disinfected to eliminate the deterioration of the contents by the bacteria.

WO 2009/123445 discloses an animal interaction system for milking, feeding and/or selecting animals. In the system, UV-light irradiates a part of the system which, in use, comes into contact with an animal, for killing bacteria, spores and/or fungi present on the part of the system and/or the UV-light can irradiate a part of an animal present in the proximity of the system. The system may be an apparatus for milking animals that is provided with a teat cup.

SUMMARY

It is an object of the invention to provide a simple and flexible solution for providing UV lamps for sterilization of surfaces, compared to prior art solutions.

According to a first aspect, the invention relates to a UV lamp having an axial dimension normal to a cross-section having a cross-sectional area with a ratio of the axial dimension to the cross-sectional area configured such that the UV lamp has a longitudinal shape, the UV lamp comprising: a first axial conductor separated from a second axial conductor by an electrically insulating material, at least one of the first axial conductor and the second axial conductor defining an outer surface, a light emitting diode (LED) capable of providing light at a wavelength in the range of 100 nm to 400 nm, the LED having a first electrical terminal electrically connected to the first axial conductor and a second electrical terminal connected to the second axial conductor; wherein the LED is mounted to emit light from the outer surface.

The UV lamp has a substantially longitudinal shape. In the context of the invention a "longitudinal shape" means that the axial dimension is longer than the cross-sectional dimension. However, it is also contemplated that the axial dimension may be equal to or smaller than the cross-sectional dimension. For example, the UV lamp may also be defined by the ratio of the axial dimension to the cross-sectional area, e.g. the ratio of the axial dimension to the cross-sectional area may be in the range of 0.1 cm/cm$^2$ to 1000 cm/cm$^2$. Exemplary dimensions comprise an axial dimension, or "length", in the range of 1 cm to 50 cm, and a cross-sectional dimension, or "width", in the range of 2 mm to 100 mm. For example, in one embodiment the length is 30 cm and the width 50 mm. In another embodiment the width is 10 mm and the length 10 cm. The cross-section of the UV lamp is not limited, and it may e.g. be circular, oval, square, or triangular.

The longitudinal shape of the UV lamp makes it suitable for the irradiation of the interior of objects and surfaces having a longitudinal or oblong shape, in particular the UV light emitted from the UV lamp can kill bacteria, germs, spores, such as bacterial or fungal spores, viruses thereby sterilizing the surface. The longitudinal shape of the UV lamp allows the UV lamp to be inserted into interior sections of containers, pipes, ducts, or the like that are difficult to reach. Since the UV lamp employs UV light for sterilization, in particular UV light from efficient LEDs, sterilization can be obtained using less energy than sterilization with steam. Thereby, a more energy efficient sterilization is obtained. A further advantage of using UV sterilization is also that potentially harmful or irritating chemicals may be avoided e.g. in teat milking cups and thereby avoiding potential exposure of animals and/or users to chemicals.

The UV lamp has an outer surface. The outer surface is provided by at least one of the first axial conductor and the second axial conductor, but the outer surface may also be defined, at least in part, by the electrically insulating material. For example, the UV lamp may have a cylindrical shape so that one of the first axial conductor and the second axial conductor, e.g. the first axial conductor alone, defines the outer surface. However, it is also possible for the outer surface to be defined by both the first axial conductor and the second axial conductor. For example, the UV lamp may be cylindrical and a section, e.g. 10% to 90%, of the perimeter of the cylinder is defined by the first axial conductor and the remaining part of the perimeter is defined by the second axial conductor, or vice versa. Part of the electrically insulating material may also be located at the outer surface, so that the outer surface is partly defined by the electrically insulating material. For example, the electrically insulating material may have a cylindrical shape with the first axial conductor being located on the outer surface of the cylindrical electrically insulating material and the second axial conductor being located on the inner surface of the cylindrical electrically insulating material, or vice versa. Thus, the outer surface can be defined by the electrically insulating material and one of the first axial conductor and the second axial conductor.

Correspondingly, the UV lamp may have an axial hollow interior, where at least one of the first axial conductor and the second axial conductor defining an inner surface. Thus, the UV lamp may have a cylindrical shape so that one of the first axial conductor and the second axial conductor, e.g. the first axial conductor alone, defines the inner surface. However, it is also possible for the inner surface to be defined by both the first axial conductor and the second axial conductor. For example, the UV lamp may be cylindrical and a section, e.g. 10% to 90%, of the perimeter of the cylinder is defined by the first axial conductor and the remaining part of the perimeter is defined by the second axial conductor, or vice versa. Part of the electrically insulating material may also be located at the inner surface, so that the inner surface is partly defined by the electrically insulating material. For example, the electrically insulating material may have a cylindrical shape with the first axial conductor being located on the outer surface of the cylindrical electrically insulating material and the second axial conductor being located on the inner surface of the cylindrical electrically insulating material, or vice versa. Thus, the inner surface can be defined by the electrically insulating material and one of the first axial conductor and the second axial conductor.

By having the LED mounted to emit light from the outer surface, the lamp may be configured to irradiate a surface arranged at a distance from the outer surface. In general, it is advantageous that the distance from the surface to be irradiated and the outer surface of the UV lamp is as low as possible, and in a specific embodiment the cross-sections of the UV lamp are selected based on the intended use of the UV lamp. For example, in a specific embodiment the UV lamp is for disinfecting or sterilizing the inner surface of a teat cup of a milking machine and the UV lamp has a generally circular cross-section with a diameter in the range of 5 mm to 30 mm, e.g. 15 mm to 30 mm. The light emitted by the LED may generally be considered as a point source light source. The dose which is dependent on the intensity of the light source is therefore substantially inversely proportional to the distance from the source. It is therefore generally preferred to keep the distance between the UV lamp and the surface to be sterilized as low as possible. The distance is preferably less than 10 cm, more preferably less than 5 cm, and most preferably less than 3 cm.

According to a second aspect, the invention relates to a UV lamp having an axial dimension normal to a cross-section having a cross-sectional area with a ratio of the axial dimension to the cross-sectional area configured such that the UV lamp has a longitudinal shape, the UV lamp comprising: —a first axial conductor separated from a second axial conductor by an electrically insulating material, at least one of the first axial conductor and the second axial conductor defining an inner surface, an axial hollow interior, an inlet opening and an outlet opening in the outer surface adapted to allow fluid communication from the inlet opening to the outlet opening via the hollow interior, and a flushing arrangement adapted to provide a fluid to the inlet opening; a light emitting diode (LED) capable of providing light at a wavelength in the range of 100 nm to 400 nm, the LED having a first electrical terminal electrically connected to the first axial conductor and a second electrical terminal connected to the second axial conductor; wherein the LED is mounted to emit light from the inner surface towards the axial hollow interior.

By having a UV lamp configured to emit light from its inner surface, it allows for the of fluids passing through the axial hollow interior from the inlet opening towards the outlet opening.

An advantage of the configuration of the UV lamp according to the invention is that a high concentration of LEDs per $cm^2$ may be achieved in the surface, whether the inner surface or the outer surface when the UV lamp has an axial hollow interior, or when the UV LEDs are located on the outer surface of the embodiment not having an axial hollow interior.

In some embodiments, the inner surface contains at least 1 LED per $cm^2$.

In some embodiments, the inner surface, or the outer surface, is capable of providing light at a wavelength in the range of 100 nm to 400 nm of at least 1 $mW/cm^2$.

This may allow irradiating a fluid passing by the LEDs from the inlet opening to the outlet opening with a dose in the range of 10 $mJ/cm^2$ to 20 $mJ/cm^2$, e.g. 2 $mJ/cm^2$ to 50 $mJ/cm^2$. The length between the inlet opening and the outlet opening may be in the range 0.1 m to 5 m, e.g. 0.5 m to 2 m. The dose may be sufficient to reduce the amount of live microbes, e.g. bacteria, virus particles, algae, spores, fungal spores, etc., with 90% or more. In the context of the invention, a 90% reduction of live microbes is considered a disinfecting treatment. However, the UV lamps of the invention may also reduce the amount of live microbes with more than 90%, e.g. the amount of live microbes may be reduced with at least 99% and up to 100%, e.g. in a fluid passed through the axial hollow interior. In the context of the invention, a 99% reduction of live microbes is considered a sterilizing treatment. The first axial conductor and/or the second axial conductor provides a heat sink allowing UV LEDs to be positioned close to each other so that a correspondingly high UV dose is available from the UV lamps, i.e. the UV lamps of any aspect of the invention. This allows that sterilization can be obtained with a limited length of the UV lamp having UV LEDs on the inner surface of an axial hollow interior.

The diameter of the inlet opening and the outlet opening may be in the range of 50 mm to 300 mm. This may allow for a flow in the range 0.5 $m^3/h$ to 10 $m^3/h$. A fluid such as water may thereby be passed through the axial hollow interior and be disinfected or sterilized when exiting the axial hollow interior from the outlet opening. The UV lamp may thereby be used e.g. to disinfect or sterilize the water in a pond, a pool, a tank, or a tap. The flow for disinfecting or sterilizing a fluid, e.g. with a reduction of at least 99% of the live bacteria cells density, is preferably in the range of 0.5 $m^3/h$ to 10 $m^3/h$, e.g. when the axial hollow interior is cylindrical and has a diameter in the range of 50 mm to 300 mm. The diameter may, however, be in the range of 10 mm to 500 mm. The fluid passed through the axial hollow interior may be provided by means of the flushing arrangement. This may e.g. be by using a propeller, an external pump, or natural water flow from the water source such as with a tap or natural current.

In some embodiments, the inner surface of the UV lamp is made of a reflective material. When the LEDs emit light from the inner surface, the reflective inner surface may reflect the light waves, whereby the killing of microbes can be improved, and the UV lamp may be shorter than without the reflective inner surface. The material of the inner surface may for example be aluminium or a reflective coating. In an embodiment, the inner surface has a reflective surface and the UV lamp has a length in the range of 0.2 m to 2 m, e.g. 0.5 m to 1.5 m.

The UV lamp according to the second aspect may e.g. be used in aquaculture or aquafarming, such as in fish farms. Fish in aquaculture are very exposed to diseases and bacteria. It is therefore important to keep the water quality in the ponds to a certain level of cleanliness with regard to bacteria. The UV lamp may for example be placed after a filtering element which filters the coarse particles. An example of a UV lamp may be a UV lamp having an axial dimension of 1 m and a diameter of 10 cm. Such a UV lamp may sterilize water with a flowing speed of 1.5 m³/h i.e. 5 cm/s. The dose that the water is exposed to may therefore be 15 mJ/cm².

The UV lamp according to the second aspect may also be used for disinfecting or sterilizing air, e.g. as part of an air conditioning system. For example, the UV lamp according to the second aspect can be used in an air supply system for the food industry, a microbiology lab or anywhere sterile air is needed.

The axial conductors may have any shape as desired. In its simplest form, the axial conductors, e.g. the first axial conductor, the second axial conductor, and/or both axial conductors, are rod shaped. The electrically insulating material may likewise be shaped as a rod. For example, the axial conductors may be integrated in a rod shaped electrically insulating material. In another embodiment, the electrically insulating material has a cylindrical shape where the electrically insulating material forms a wall surrounding an axial hollow interior. The axial conductors, e.g. in the form of rods, may be attached to either side of the wall, e.g. the interior or the exterior side of the wall. It is also contemplated to integrate the rod shaped axial conductors in the wall of the cylinder.

The UV lamp of the invention comprises a first and a second axial conductor. What is understood by the term "axial", is that the conductor follows the axial dimension of the UV lamp. The length of the axial conductors may be equal to the length of the UV lamp or the axial conductors may be shorter than the UV lamp. It is generally preferred that the first and the second axial conductors are of the same approximate length. For example, the ratio of the length of the first axial conductor to the second axial conductor may be in the range of 0.8 to 1.2.

The axial conductors are generally rigid and provide structure to the UV lamp, although it is also contemplated that the axial conductors are flexible, e.g. in the form of wires or cables, and rigidity is provided by the electrically insulating material. It is further contemplated that the UV lamp comprises two or more rigid sections joined by hinges or the like.

The axial conductors provide power to the LED, and the first axial conductor may function as a cathode and the second axial conductor may function as an anode or vice versa. The first and second axial conductors shall not be in direct contact with each other at any place in the UV lamp, so that short circuits cannot happen in the electric circuit and damage to components of the UV lamp is prevented.

The cross-sectional shape of the UV lamp may be selected freely, but in an embodiment the cross-section is substantially circular and symmetrical about an axis of rotation of the lamp. The axis of rotation of the lamp may be perpendicular to the axial dimension of the lamp.

The first axial conductor may be concentric to the second axial conductor, or vice versa, e.g. in the axial dimension of the lamp. The term concentric may also be understood as coaxial. For example, the first axial conductor may have the shape of a rigid rod, which is surrounded by the electrically insulating material, e.g. arranged as a concentric layer, which in turn is concentrically surrounded by the second axial conductor. When either of the axial conductors or the electrically insulating material is "concentric" or "co-axial" the material can be said to be in a "layer".

The UV lamps of the invention may have an axial hollow interior such as a hollow cylinder. For example, the UV lamp may have a generally cylindrical shape where the first axial conductor, the electrically insulating material and the second axial conductor form layers of the cylinder so that the first axial conductor is separated from the second axial conductor by the electrically insulating material. When the UV lamps are cylindrical, the cylinder provides an axial hollow interior, and the LEDs may be located on the outer surface of the cylinder, i.e. the LEDs emit light away from the longitudinal axis of the UV lamp, or the LEDs may be located on the inner surface of the cylinder, i.e. the LEDs emit light toward the longitudinal axis of the UV lamp.

When the UV lamp has an axial hollow interior, it will also have an inlet opening and an outlet opening in the outer surface adapted to allow fluid communication from the inlet opening to the outlet opening via the hollow interior. Thus, a fluid can be passed through the hollow interior of the UV lamp, and the UV lamp has a flushing arrangement adapted to provide a fluid to the inlet opening. The UV lamp having a hollow interior may have UV LEDs on the inner surface for emitting UV light from the inner surface toward the axial hollow interior, or the UV lamp having a hollow interior may have UV LEDs on the outer surface for emitting UV light from the outer surface toward an inner surface of a container, a pipe, a duct, or the like into which the UV lamp has been inserted. When the UV lamp has UV LEDs in the inner surface the fluid in the UV lamp can be disinfected or sterilized. The fluid may be an aqueous liquid or air. When the UV lamp has UV LEDs in the outer surface the fluid in the UV lamp can be used to wash the surface to be disinfected or sterilized by the UV LEDs on the outer surface of the UV lamp.

In another exemplary embodiment the first and second axial conductors, and the electrically insulating material, are shaped as concentric cylinders. These concentrically cylindrical layers may also be referred to as a hollow shell. In particular, the electrically insulating material may also be shaped as a cylinder, which may be positioned between the first and second axial conductors, and therefore also be concentric with the first and second axial conductors. The first axial conductor, the second axial conductor, and the electrically insulating material may thereby be arranged in a "sandwich structure", where the first axial conductor, the second axial conductor, and the electrically insulating material are concentric, and the electrically insulating material separates the first axial conductor and the second axial conductor. By having the first and second axial conductors, and the electrically insulating material in a layered, concentric structure, a compact and simple design may be provided.

The first and second axial conductors may be made from the same materials or of different electrically conducting materials. The electrically conducting materials may be one or more of aluminium, titanium, copper, steel, stainless steel, silver, gold, graphite, brass, silicon and conducting polymer or a composite material. These materials may also be used for further elements of the invention.

The thickness of each of the axial conductors may be up to 50 mm, such as up to 40 mm, such as up to 30 mm, such as up to 20 mm, such as up to 10 mm, such as up to 5 mm, such as up to 1 mm, such as 0.1 to 50 mm, such as 0.4 to 1 mm. When an axial conductor is arranged in a concentric layer it is preferred that the thickness of the layer, e.g. the thickness in a radial dimension, is in the range of 0.1 mm to 2 mm.

In an embodiment, one or both of the axial conductors has/have been extruded from a metal, e.g. from aluminium, magnesium, copper, titanium, or steel. It is also possible that the electrically insulating material is prepared by extrusion. In a specific embodiment, the axial conductors and the electrically insulating material are co-extruded simultaneously, e.g. for the UV lamp to be extruded into its final, or nearly final, shape.

In an embodiment, one or both of the axial conductors are prepared from aluminium, magnesium or titanium, which has subsequently been anodised to provide an electrically insulating oxide layer. In a preferred embodiment, one or both of the axial conductors has/have been extruded from aluminium, magnesium or titanium, which has subsequently been anodised. Metals may be anodised to provide the metals with an oxide layer on the surface. Such an oxide layer may have a thickness of at least 10 μm.

The first and/or second axial conductors may be divided into one or more separate zones such that different electrical potentials may be defined.

The electrically insulating material may comprise a foamed material (open and/or closed celled) and/or a reinforced material such as a fibre glass material. The electrically insulating layer may be made of a polymer material such as amorphous plastic materials (e.g. polyvinylchloride, polycarbonate and polystyrene) or crystalline plastic materials (e.g. Nylon, polyethylene and polypropylene), or wood.

The electrically insulating material may define a honeycomb structure.

In some embodiments the UV lamp further comprises a power supply capable of providing a voltage between the first axial conductor and the second axial conductor.

The power supply may use any standardised voltage, e.g. in the range of 5 V to 12 V, although higher voltages, e.g. 24 V, 36 V or 48 V, are also contemplated. It is preferred that the power supply provides a direct current of constant voltage. The power supply may be connected to the grid in order to provide power to the UV lamp. In an alternative embodiment the power supply may comprise a battery. By having a battery, the UV lamp may be transportable and is not dependent on a stationary power supply. Furthermore, the UV may then be movable and may be arranged to sterilize surfaces that are difficult to access with a stationary installation. When present, the power supply supplies power to the LEDs via the axial conductors, and thereby removes the need for separate wiring to each LED or electrical component, thus providing a simple and flexible system. The UV lamp may comprise a circuit board carrying the LED. The circuit board may be positioned between the LED and one of the axial conductors. Thereby an improved thermal connection to a heat sink of the LED may be obtained. Because the heat is effectively led away from the LED, the durability of the LED is extended and the performance over time is improved.

The outer surface may be defined by the first axial conductor or by the second axial conductor. For example, the outer surface may be defined only by the first axial conductor, or only by the second axial conductor. However, it is also contemplated that the outer surface is defined by a combination of the first axial conductor and the second axial conductor, e.g. that 50% of the outer surface is formed by the first axial conductor and that the remaining 50% of the outer surface is formed by the second axial conductor. Furthermore, it is also contemplated that the outer surface is, at least partly, formed by the electrical insulating material. For example, the outer surface may be formed only by the electrical insulating material, or by both the first and second axial conductors and the electrical insulating material, or by one of the first and second axial conductors together with the electrical insulating material. By having one or more axial conductors defining the outer surface of the UV lamp, the lamp may have a substantially cylindrical shape. By having the outer surface of the UV lamp defined by the axial conductors and/or the insulating material, the UV lamp may be very compact, and further elements needed in other type of UV lamps may be avoided. The outer surface may be facing in the opposite direction than an inner surface of the axial hollow interior of the UV lamp. Generally, the outer surface is facing the environment surrounding the UV lamp. The outer surface may have a surface area that is at least 25%, 50%, 100%, 200%, or 500% larger than the surface area of the inner surface.

By having an LED capable of providing light at a wavelength in the range of 100 nm to 400 nm, the UV lamp may be able to sterilize surfaces by irradiating said surface by providing a suitable UV dose to the surface. Light with a wavelength in the range of 100 nm to 400 nm is known as ultraviolet light, which is abbreviated as "UV". The wavelength range of 100 nm to 400 nm comprise the UVA, UVB, and UVC spectrum which are known to be germicidal. A preferred wavelength is in the range of 100 nm to 280 nm, i.e. UVC. In the context of the invention an LED may be a single LED or the term "LED" may refer to a group of serially connected LEDs. In a specific embodiment, the LED is a series, e.g. a series of 4 or 8 LEDs, and the series of LEDs is placed on a circuit board. The LED may be surface mounted on the circuit board.

The term "electrical terminal" is to be understood as a point or element for entry of power and/or data. The electrical terminal may be e.g. a positive or a negative electric pole.

When the UV lamp has a layer of an axial conductor, e.g. the first axial conductor, surrounding a layer of the electrically insulating material, which in turn surrounds an axial conductor, e.g. the second axial conductor, which may be rod shaped or cylindrical, it is preferred that the LED is mounted on the UV lamp in a recess extending through the outer surface e.g. the first axial conductor and the electrically insulating material, whereby the recess allows access to the inner surface e.g. the second axial conductor. The first electrical terminal of the LED may thereby be electrically connected to the first axial conductor and the second electrical terminal connected to the second axial conductor, when the LED is mounted in the recess. The embodiment should not be limited to have the first axial conductor as the outer layer and the second axial conductor as the inner layer, they may also be interchanged.

The LED may be mounted in the recess as desired, as long as the first electrical terminal is electrically connected to the first axial conductor and the second electrical terminal is connected to the second axial conductor. For example, the LED may be soldered or glued to the axial conductors. In a specific embodiment, the LED is placed on a circuit board, e.g. the LED is surface mounted on the circuit board, and the circuit board is placed in the recess. The LED, especially when the LED is mounted on a circuit board, the UV lamp may comprise a coupling unit for retaining the LED. The coupling unit may be a locking ring, which may be press-fitted, coupling magnetically, or have an inner screw thread matching an outer screw thread of the LED. The number of recesses in the UV lamp may be scaled with the number of LEDs mounted on the UV lamp.

In some embodiments the UV lamp further comprises an axial hollow interior, an inlet opening and an outlet opening in the outer surface adapted to allow fluid communication from the inlet opening to the outlet opening via the hollow interior, and a flushing arrangement adapted to provide a fluid to the inlet opening. In a preferred embodiment the axial conductors and the electrically insulating material are arranged concentrically to have a cylindrical shape, which provides the UV lamp with the axial hollow interior. In this embodiment the UV lamp is generally described as a "cylinder". The cylinder preferably has an inner diameter in the range of 1 mm to 25 mm.

In the context of the invention a "flushing arrangement" generally comprises a supply of fluid to the inlet opening, and the flushing arrangement may be arranged in the axial hollow interior, or it may be arranged externally to the axial hollow interior. For example, the flushing arrangement may alternatively also be arranged e.g. on a side of the UV lamp by being attached to a portion of the outer surface. The flushing arrangement is in fluid communication with inlet opening and thus also the outlet opening. The flushing arrangement may comprise a reservoir, a pump, e.g. a pump capable of supplying liquid to the inlet opening at a pressure in the range of 2 bar to 20 bar, tubing connections, and/or a regulator with a valve. The flushing arrangement may be connected to an external fluid source providing for example water, rinsing solution, alcohol, or disinfecting solution. The axial hollow interior may also be arranged to be flushed by the flushing arrangement.

When the UV lamp has a flushing arrangement adapted to provide a fluid to the inlet opening of a cylinder, the same instrument, i.e. the UV lamp of the invention, can be used to remove debris, e.g. residual milk in a teat cup, before and/or after sterilizing a surface. By combining cleaning, i.e. flushing the surface with a liquid, with UV irradiation of the surface a more efficient sterilization is obtained. The substantially longitudinal shape of the cylinder and the UV lamp of the invention allows the UV lamp to be inserted into tubes and the like having difficult access. Thus, the UV lamp of the invention having a flushing arrangement is particularly suited for cleaning and sterilizing the inner surface of tubes or the like, which inner surfaces are otherwise difficult to reach. Furthermore, debris, especially milk residues from the milking of a cow, may be opaque to UV light so that the flushing arrangement allows that UV sterilization is performed in e.g. a teat cup.

When the UV lamp has a flushing arrangement adapted to provide a fluid to the inlet opening of a cylinder and UV LEDs on the inner surface of the axial hollow interior, the fluid in the axial hollow interior can be disinfected or sterilized.

The inlet opening, regardless of the location of the UV LEDs, e.g. whether the UV LEDs are located on the inner surface or the outer surface of the UV lamp, may be placed at any axial position of the cylinder, but the inlet opening is preferably near or at a first end of the cylinder. Likewise, the outlet opening may be positioned anywhere on the cylinder. In general, the outlet opening is "downstream" of the inlet opening. It is preferred that when the UV LEDs are on the outer surface, the cylinder has a single inlet opening but in an embodiment the cylinder has a plurality of outlet openings. When the UV LEDs are on the inner surface, it is preferred that the cylinder has a single inlet opening and a single outlet opening, e.g. at an opposite end from the inlet opening. The outlet opening is or the outlet openings are generally of a smaller cross-sectional area than the inlet opening. For example, the inlet opening may be circular and have a diameter in the range of 1 mm to 25 mm, e.g. at the first end of the cylinder, and the cylinder may have a plurality, e.g. 5 to 20, outlet openings each with a diameter in the range of 0.1 mm to 2 mm. When the total cross-sectional area of the outlet openings is smaller than the cross-sectional area of the inlet opening, e.g. when the ratio of the total cross-sectional area of the outlet openings to the cross-sectional area of the inlet opening is in the range of 0.01 to 0.1, liquid can be ejected from the outlet openings at sufficient velocity to remove debris from a surface in a cleaning procedure.

In a preferred embodiment, the cylinder has a plurality of outlet openings, e.g. 8 to 12 outlet openings, with a diameter in the range of 0.5 mm to 1 mm, which outlet openings are located at or near the opposite end of the cylinder having the inlet opening. The plurality of outlet openings is preferably located along the circumference of the cylinder, e.g. the outlet openings are distributed evenly along the circumference of the cylinder. When the outlet openings are distributed along the circumference of the cylinder at or near the opposite end of the cylinder it is possible to flush the complete inner surface of an item to be sterilized, e.g. a teat cup.

The axial hollow interior may accommodate a tube or a hose, or the inlet opening may be in fluid communication with a tube or hose. to allow fluid communication from the inlet opening to the outlet opening. By having a flushing arrangement, the UV lamp may be arranged to flush a surface before and/or after the sterilization of said surface to be sterilized. The shape of axial hollow interior may be defined by the axial conductors and/or the insulating material. By having the axial hollow interior defined by the axial conductors and/or the insulating material, the lamp may have a further compact shape, as the flushing arrangement may be arranged inside the axial hollow interior. The axial hollow interior has a smaller cross sectional area than the cross sectional area of the lamp. Further, the axial hollow interior may have a length in the axial dimension direction matching the axial dimension of the lamp. The axial hollow interior may alternatively only extend at a portion of the axial dimension of the lamp.

In a further exemplary embodiment, the first and second axial conductors may be shaped as two half cylindrical hollow shells, where the electrically insulating material is positioned between the two half cylindrical hollow shells along the axial dimension, such that the first and second axial conductors are separated from each other but are still adjacent. The first and second axial conductors may be arranged such that they form a substantially complete cylindrical hollow shell. The two half cylindrical hollow shells may be formed by cutting a complete cylindrical hollow shell along the axial dimension. Alternatively, a complete hollow cylindrical shell may be cut along the cross-sectional dimension to form two complete cylindrical hollow shells, which are then separated by an electrically insulating material along the cross-sectional dimension. In this embodiment, both the first and second axial conductors, and the electrically insulating material are defining the outer surface of the UV lamp. By positioning the first and second axial conductors, and the electrically insulating material in the same plane i.e. not concentric to each other the hollow interior of the UV lamp may be used solely for accommodating other parts, such as e.g. the flushing arrangement.

In some embodiments the first axial conductor forms the outer surface, said first axial conductor being continuous along a perimeter of the cross-section at a fraction of the axial dimension in the range of 10% to 100%. It is preferred that the first axial conductor is continuous along the perimeter at a fraction of the axial dimension of at least 50%.

What is understood by the term "continuous" is that the first axial conductor is made out of one piece. Thus, the continuous section can also be described as a tubular section. The first axial conductor is still considered to be continuous when having recesses arranged to mount LEDs, in particular when the UV lamp comprises UV transparent, water tight windows at the recesses. Likewise, when the UV lamp has an axial hollow interior with outlet openings in the outer surface the outer surface, e.g. the first axial conductor, is also considered to be continuous. The first axial conductor may define the outer surface, and the outer surface may therefore also in some embodiments be considered as continuous along the perimeter of the cross-section. The second axial conductor may also be continuous along the perimeter of the cross-section at a fraction of the axial dimension, whereby the inner surface of the UV lamp is also continuous, e.g. along a perimeter of the cross-section at a fraction of the axial dimension in the range of 10% to 100%. For example, in an embodiment the first and the second axial conductors are concentric tubes with a likewise tubular electrically insulating material between the axial conductors. An advantage of having a continuous section, e.g. a tubular section, of the first or the first and also the second axial conductor is that the handling of liquids is made easier by preventing substantially the penetration of liquids through the elements of the UV lamp. For example, by having a continuous axial conductor defining the inner surface of the UV lamp, the inner surface is water/liquid tight, and the risk of short circuiting LEDs or other components in the UV lamp is reduced. In a further embodiment, the inner surface of the UV lamp may be an anodised axial conductor, e.g. the second axial conductor, providing thereby corrosion resistance. A further advantage is that the inner axial conductor defining the inner surface, may improve heat transfer from the LEDs by functioning as heat sinks for the LEDs. Additionally, the heat transfer may be further improved by having the flushing arrangement where liquid, especially an aqueous liquid, provides a highly efficient heat sink for the LEDs cools the inner surface of the UV lamp with water, having a high heat capacity.

The fraction of the axial dimension which is not the outer surface formed by the first axial conductor may e.g. be a housing, a cover part, or a base of the lamp. The fraction of the axial dimension which is not the outer surface formed by the first axial conductor may be connected to a support element, such as e.g. a table, a rod, a stand or the like.

In some embodiments the UV lamp further comprises a window transparent to light at a wavelength in the range of 100 nm to 400 nm, the window being adapted to provide a water tight cover for the LED and let light emitted from the LED through. In the context of the invention, "water tight" is too be understood broadly so that the water tight lid cover will also prevent penetration of other liquids. In particular, "water tight" means that penetration of any liquid used with the invention is prevented. In the context of the invention water tight may also be referred to as "liquid tight" and the two terms may be used interchangeably. Exemplary liquids comprise water, aqueous solutions, e.g. aqueous solutions of surfactants, detergents, soaps, salts, etc., or organic solvents, e.g. alcohols, or combinations of aqueous solutions and organic solvents. The water tightness may follow any standardised classification, and the UV lamp may for example have a water tightness of IP4, IP5, IP6, IP7 or better according to the international standard IEC 60529.

The window may be made of any material transparent to light at a wavelength of 100 nm to 400 nm. Such a material may e.g. be a polymer, quartz, fused silica, calcium fluoride, or magnesium fluoride, optionally covered with a protective layer preventing deterioration of the window by surrounding solutions. In the context of the invention, the solutions used e.g. for the flushing, may comprise salts that may attack the surface of the window and potentially deteriorate the transparency of the window. This may be avoided with a protective layer. By having a window adapted to provide a water tight cover for the LED and let light emitted from the LED through, the LED does not need an integrated protective layer or film to protect the LED from the environment it is used in. This also makes the lamp suitable for wet environments. The window may be an integrated part of an axial conductor or attached to an axial conductor. The window may thereby form part of the outer surface of the lamp.

The window may also work as a lens or optic for the LED in order to collimate or spread the light emitted from the LED.

In some embodiments the window is arranged as or is integrated in a housing for the UV lamp. The housing may be made from the same materials as the window to provide transparency to UV light. The housing may comprise sections of UV transparent materials at the locations of the LEDs.

By having a housing, the UV lamp may be further protected from the environment where the lamp is to be used. This may for example be a wet environment. The housing may be connected to a support element, such as e.g. a table, a rod, a stand or the like, whereby the lamp may be arranged in fixed mounted position and the surfaces to be sterilized are brought to the UV lamp. The housing may be formed entirely or partially by the axial conductors and/or insulating material. The recesses for mounting the LEDs may also extend through the housing.

In some embodiments the UV lamp comprises a plurality of LEDs arranged so that light is emitted at a fraction in the range of 50% to 100% of a perimeter of the cross-section. A plurality of LEDs may be distributed along the length of the UV lamp. When the axial conductors and the electrically insulating layers are concentric, the UV lamp allows flexible positioning of the LEDs both with respect to the actual position and also the number of LEDs since the large cross-sections of the axially conducting layers have insignificant electrical resistance. For example, when the axially conducting layers have a thickness in the range of 0.5 mm to 2 mm the resistance will be insignificant and moreover the heat conducting nature of the axially conducting layers, e.g. when made from aluminium, provides that any number of LEDs can be positioned at any location on the UV lamp. For example, the LEDs may be located in recesses through the outer axial conductor and the electrically insulating layer.

By having LEDs arranged such that light is emitted at a fraction in the range of 50% to 100% of a perimeter of the cross-section, a surface positioned along the perimeter of the cross-section and the axial dimension of the UV lamp, may be irradiated in the range of 50% to 100%. The surface to be sterilized may be substantially concentric with the UV lamp, e.g. the surface may be the inner surface of a teat cup, whereby substantially the entire said surface may be irradiated and sterilized at the same time. The shape of the object to be sterilized may be substantially cylindrical with a hollow interior, and may thereby fit substantially in shape such that the UV lamp may be inserted in the object to be sterilized.

In case more LEDs are present, circuit boards are preferably positioned under each of the LEDs. Thus each LED is connected or associated with its own circuit board. The LEDs are preferably not mounted on one common circuit board. By associating each LED with its own circuit board and leading the power through the axial conductors a low voltage drop is obtained. If all LEDs were positioned on the same circuit board the cross section of the power supply lines would be much smaller and result in a greater voltage drop. Here the first and second axial conductors are forming part of the power supply lines. The first and second axial conductors generally have a greater cross sectional area than power supply lines on a circuit board.

Each circuit board is preferably 5 mm to 20 mm in diameter. The circuit board may also be rectangular, e.g. 5 mm×20 mm. The circuit board is preferably positioned in a recess together with the LED.

In some embodiments the UV lamp further comprises a power supply capable of providing a direct current between the first axial conductor and the second axial conductor, the power supply further being capable of providing a first constant voltage equal to or higher than a nominal forward voltage ($V_f$) of the LED and a second constant voltage below the nominal forward voltage ($V_f$) of the LED.

A LED will have a forward voltage ($V_f$) that is needed to power the LED and turn it on, whereas other electronic components generally have a lower minimum voltage for functioning. By having a power supply capable of providing a second constant voltage below the nominal forward voltage ($V_f$) of the LED, the lamp may have electrical components being supplied by the power supply while the LED is off.

In some embodiments the UV lamp further comprises an electronic component being operable at the second constant voltage.

Examples of electronic components are transistors, controllers, chip on boards (COB), drivers, power supplies, microphones, cameras, sensors or fans. Different electronic components may be combined in the UV lamp. A preferred electronic component is a sensor, e.g. a sensor for temperature, humidity, pH, or a camera. With a sensor or a camera, it is possible to collect data in the environment for sterilization before and/or after irradiating the surface with UV light. By collecting measurements from sensors before and/or after the irradiation and/or the flushing of a surface, the collected data may be compared e.g. before and after the irradiation and/or the flushing of a surface. The surface to be sterilized may thereby be inspected based on several parameters, and the quality of the sterilization and/or the flushing may be controlled and assessed. The measurements and/or images collected from the sensors and/or camera may indicate if the sterilization and/or the flushing have/has been satisfying with respect to standard measurements defining a quality control.

A further advantage of having a power supply capable of providing a second constant voltage below the nominal forward voltage ($V_f$) of the LED, may be that an electronic component such as sensor or a camera may be able to function while the LED is off, and thereby collecting measurements and/or images independently from the LED, and may for example not be disturbed by the LED irradiating the surface.

The UV lamp may comprise a controller adapted for communication of data signals via at least one of the axial conductors.

The controller may also be positioned outside the lamp or each electronic component may be provided with its own controller, preferably positioned in the vicinity of the electronic component.

In some embodiment the data signals are transmitted via the first axial conductor and/or the second axial conductor by means of Direct Current Power Line Communication (DC PLC). Thus there is no separate layer for data communication, but instead the data is transmitted on the same layer as the power to the LED. This dispenses with the need for separate wiring for data transfer.

The UV lamp may further comprise a third axial conductor, preferably positioned between the first axial conductor and the second axial conductor, where the third axial conductor is adapted to transmit the data signals. By adding a third axial conductor the data transfer is separated from the power transfer. Thereby any glitch or noise over the power line does not disturb the data transfer. Additionally, more layers may be added to the structure such that the first axial conductor or the second axial conductor are not necessarily the outermost layers. Further layers may also be added between the first axial conductor or the second axial conductor.

In a particularly preferred embodiment, the UV lamp comprises an inner, tubular, e.g. of a circular cross-section, axial conductor surrounded by a tubular, concentric layer of the electrically insulating material, which is surrounded by a tubular, concentric layer of the axial conductor representing the outer surface. The layers in this embodiment, i.e. the first and the second axial conductors and the electrically insulating layer, may also be referred to as a "tube" and the layers may have the same length and be continuous along the perimeter of the cross-section from an inlet opening near or at a first end of the cylinder to at least 80% of the length of the layers. The inner diameter of the tube may be in the range of 1 mm to 15 mm. The inner tubular axial conductor, and optionally also the outer axial conductor, is preferably made from an anodised metal, e.g. aluminium, magnesium or titanium. In this embodiment, the UV lamp, i.e. the tube, has a plurality of outlet openings, e.g. 8 to 12 outlet openings, distributed along the perimeter of the tube at a distance from the first end of 80% to 95% of the length of the tube. A plurality of LEDs is mounted in recesses through the outer layer of the axial conductor and the electrically insulating layer. The LEDs may be distributed along the length of the tube and arranged along the perimeter of the tube. This embodiment provides a completely watertight tube, which, when the inner surface is also anodised, is further resistant to corrosion so that the electrical or electronic components, i.e. the LEDs and other components mounted in the UV lamp are completely shielded from the water inside the tube. It is further preferred that the LEDs in the recesses are covered with UV transparent windows, e.g. of quartz glass, arranged to provide liquid tightness of at least IP4. It is further preferred that the tube has a flushing arrangement adapted to provide a fluid to the inlet opening; the flushing arrangement may comprise a pump capable of providing a liquid flow to the inlet opening at a pressure in the range of 5 bar to 15 bar.

According to a third aspect, the invention relates to a method of sterilizing a surface comprising the steps of:
  providing a UV lamp according to the first aspect of the invention, and
  irradiating the surface at a UV dose of at least 10 mJ/cm$^2$.
    Any embodiment of the UV lamp of the invention may be used in the method of the invention.

By irradiating the surface of an object at a UV dose of a least 10 mJ/cm$^2$, the live bacterial cells density at the surface may be reduced by at least 99% and up to 100%, e.g. 99.999%, i.e. the surface is sterilized. With a UV dose of at least 2 mJ/cm$^2$ the surface may be disinfected. The UV dose may also be varied to e.g. 5 mJ/cm2, 10 mJ/cm2, 15 mJ/cm$^2$, 20 mJ/cm$^2$, 25 mJ/cm$^2$, 30 mJ/cm$^2$, or more.

The method of disinfecting, e.g. sterilizing, a surface by using a UV lamp according to the first aspect of the invention may e.g. be used in the field of dairy farming and dairy production. For example, for disinfecting or sterilizing teat milking cups between the milking of each animal. Thus, in a specific embodiment the surface is the interior surface of a teat cup, and the method comprises the steps of inserting the UV lamp into the teat cup, irradiating the surface at a UV dose of at least 2 mJ/cm$^2$, e.g. at least 10 mJ/cm$^2$, and removing the UV lamp from the teat cup. In a further embodiment the UV lamp comprises an axial hollow interior, an inlet opening and an outlet opening in the outer surface adapted to allow fluid communication from the inlet opening to the outlet opening via the hollow interior, and a flushing arrangement adapted to provide a fluid to the inlet opening, and the method further comprises the step of flushing the surface, e.g. the interior of the teat cup. The flushing may be performed before the UV irradiation, after the UV irradiation or both before and after the UV irradiation. In a certain embodiment, the UV irradiation and the flushing are performed simultaneously.

By disinfecting or sterilizing the teat milking cups between the milking of each animal, the risk of transmitting diseases or infections to the next animal may be avoided or at least considerably reduced. However, with the presently available technologies sterilizing teat cups is cumbersome and typically involves application of sterilizing means, e.g. sterilizing liquids or steam, into the teat cup. Furthermore, the application of sterilizing means creates the need for removal of the sterilizing means after the sterilization. In contrast, the UV lamp of the present invention allows a much simplified sterilization procedure, which is also faster than current technologies. Moreover, the UV irradiation is more energy efficient than sterilization using steam. Thereby, the invention provides a simple way to sterilise a teat cup between each use of the teat cup for milking an animal. Several UV lamps may be used, for example if the milking apparatus has more than one teat milking cup. By matching the number of UV lamps with the number of teat milking cups, all the teat milking cups may be sterilized at the same time.

Another example is the disinfection or sterilization of the surface of food products.

The UV lamp and the method of disinfecting or sterilizing a surface may be used for any application where a surface of an object has to be disinfected or sterilized between several expositions of the surface to humans or animals, in order to avoid or reduce the risk of transmitting diseases or infections to the next human or animal exposed the surface of an object. The UV lamp of the present invention presents many advantages for the sterilization of food products. The UV lamp may for example be inserted in hollow food products e.g. as poultry or other meat pieces, and sterilize surfaces that otherwise would be difficult to reach. Additionally, the UV lamp provides a sterilization without the use of any chemicals and does not leave any contaminants on the surface or on the food product that need to be removed. The sterilization of food products may therefore involve fewer steps and may be achieved faster than current technologies.

According to a fourth aspect, the invention relates to a method of disinfecting a surface comprising the steps of: providing a UV lamp according to the first aspect of the invention, —irradiating the surface at a UV dose of at least 5 mJ/cm$^2$, and —flushing the surface by applying at least 0.2 mL/cm$^2$ of a liquid to the surface from the flushing arrangement.

The UV dose of at least 2 mJ/cm$^2$ will provide disinfection. A UV dose of at least 10 mJ/cm$^2$ will provide sterilization. The disinfection and sterilization may depend on the type of bacteria to be sterilized.

By flushing the surface after the irradiating step, impurities such as killed and dead bacteria and other debris may be flushed away. The risk of transmitting diseases or infections to the next animal in a milking process for example may be further reduced. Moreover, the quality of the milk will be increased since the number of bacteria in the milk is reduced. The surface area may be flushed with at least 0.2 mL/cm$^2$/s, preferably at least 0.3 mL/cm$^2$/s, and most preferably at least 0.5 mL/cm$^2$/s. In general, sufficient flushing can be obtained using 1 mL/cm$^2$/s. The flushing may have a duration of at least 1 s and preferably not longer than 10 s. Thus, by using the UV lamp of the present invention for cleaning a surface, e.g. the inside surface of a teat cup, a fast procedure has been made available. A typical surface area to be flushed would be approximately 30 cm$^2$, although the surface is not limited to this size. In particular, the surface may be larger than 30 cm$^2$.

The order of the flushing and irradiating steps is not relevant, and the flushing of the surface happen before or after the irradiation. A flushing step may also be performed before and after the irradiating step.

In order to improve the irradiation of the surface to be sterilized the surface and/or the UV lamp may be rotated and/or moved in a translatory movement, whereby an increased area of the surface to be sterilized may be exposed to the irradiation.

It should be understood that combinations of the features in the various embodiments and aspects are also contemplated, and that the various features, details and embodiments may be freely combined into other embodiments. In particular, it is contemplated that all definitions, features, details, and embodiments regarding the UV lamp and the methods apply equally to one another.

Reference to the figures serves to explain the invention and should not be construed as limiting the features to the specific embodiments as depicted.

BRIEF DESCRIPTION OF THE DRAWINGS

The above and/or additional objects, features and advantages of the present invention will be further elucidated by the following illustrative and non-limiting detailed description of embodiments of the present invention, with reference to the appended drawings, wherein.

DETAILED DESCRIPTION

In the following description reference is made to the accompanying figures, which show by way of illustration how the invention may be practiced.

Figure 1:
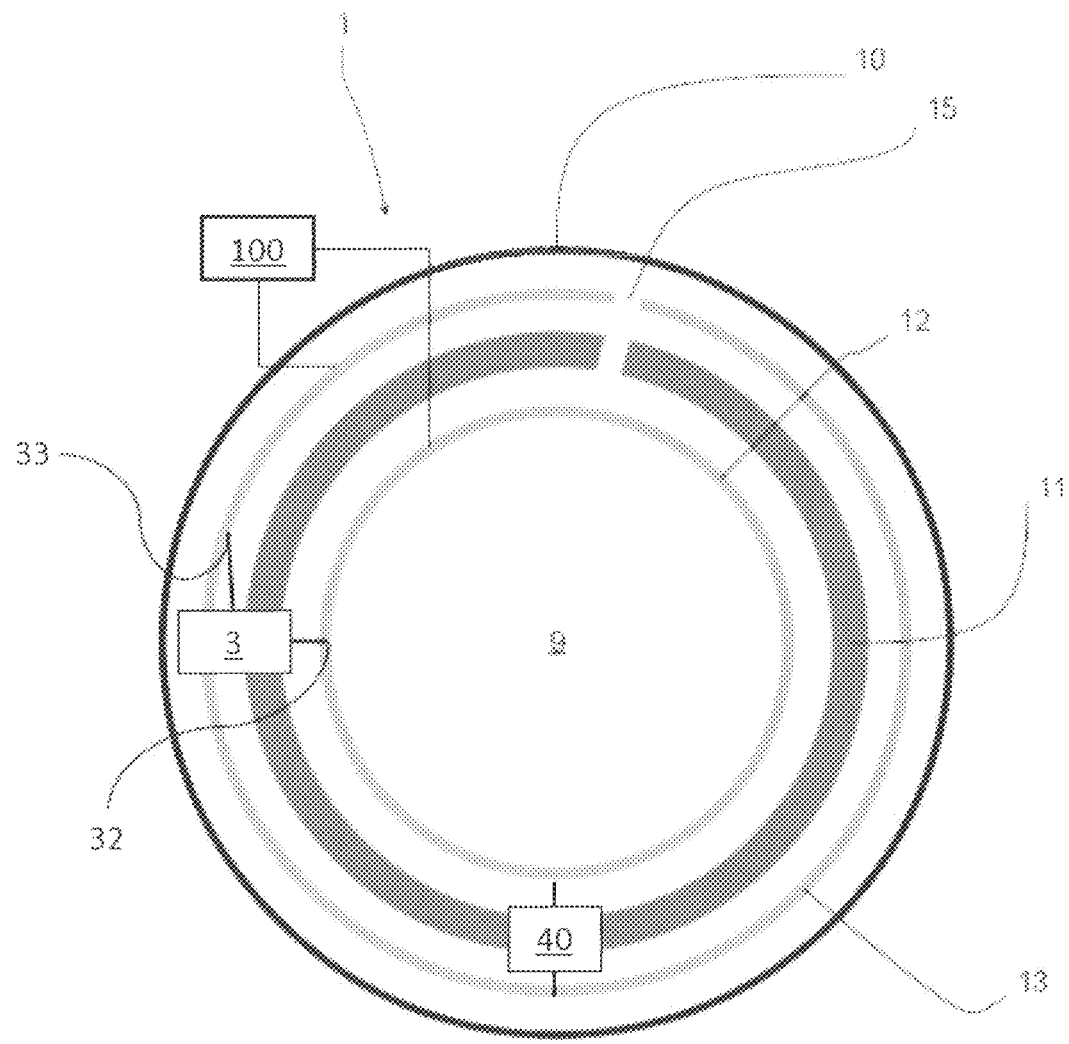
FIG. 1 shows a cross-section of a UV lamp according to an embodiment of the invention.

FIG. 1 shows a schematic cross sectional view of a UV lamp 1 according to an embodiment of the present invention. The UV lamp 1 has a circular cross section and comprises a first axial conductor 12 separated from a second axial conductor 13 by an electrically insulating material 11. In this embodiment an outer quartz glass layer 10 defines an outer surface. Alternatively, the first and/or the second axial conductor 12, 13, and optionally the electrically insulating material 11, may define the outer surface. Other type of materials may also be used and define the outer surface. The outer quartz layer 10 provides the UV lamp 1 with a window transparent to light at a wavelength in the range of 100 nm to 400 nm, the window being adapted to provide a water tight cover for the light emitting diode (LED) 3 and let light emitted from the LED 3 through. The UV lamp 1 further comprises a LED 3 capable of providing light at a wavelength in the range of 100 nm to 400 nm. The LED 3 has a first electrical terminal 32 electrically connected to the first axial conductor 12 and a second electrical terminal 33 connected to the second axial conductor 13, wherein the LED is mounted to emit light from the outer surface. A power supply 100 provides a voltage between the first axial conductor 12 and the second axial conductor 13. The UV lamp 1 further comprises an electronic component 40.

In FIG. 1 the first axial conductor 12, the electrically insulating material 11, the second axial conductor 13, and the outer surface 10 are shown for the sake of illustration separated from each other by a distance. In practice the before mentioned layers are substantially in contact with each other without any distance between them. The first axial conductor 12, the second axial conductor 13, the electrically insulating material 11 and the outer surface are concentric, the first axial conductor 12 is surrounded by the electrically insulating material 11, the electrically insulating material 11 is surrounded by the second axial conductor 13, and the second axial conductor 13 is surrounded by the outer quartz glass 10 layer defining the outer surface. The dimensions and the ratios of the layers of the UV lamp 1 have been exaggerated/emphasised in order to clearly show the layers individually in a cross sectional view, but does substantially not reflect the actual dimensions and ratios of the UV lamp 1 in practice.

In the embodiment shown in FIG. 1 the second axial conductor 13 and the electrically insulating material 11 are each provided with a through hole 15, allowing access to the inner surface 12, which is here the first axial conductor 12, from the second axial conductor 13. When aligned, the through holes 15 provide a recess (not shown). The LED 3 is thereby mounted in the recess (not shown) which is thus aligned with the through holes 15 and the first electrical terminal 32 of the LED may thereby be electrically connected to the first axial conductor 12 and the second electrical terminal 33 connected to the second axial conductor 13. Through holes 15 and recesses will typically be provided for each LED 3 or for each series of LEDs along the axial dimension.

Figure 4:
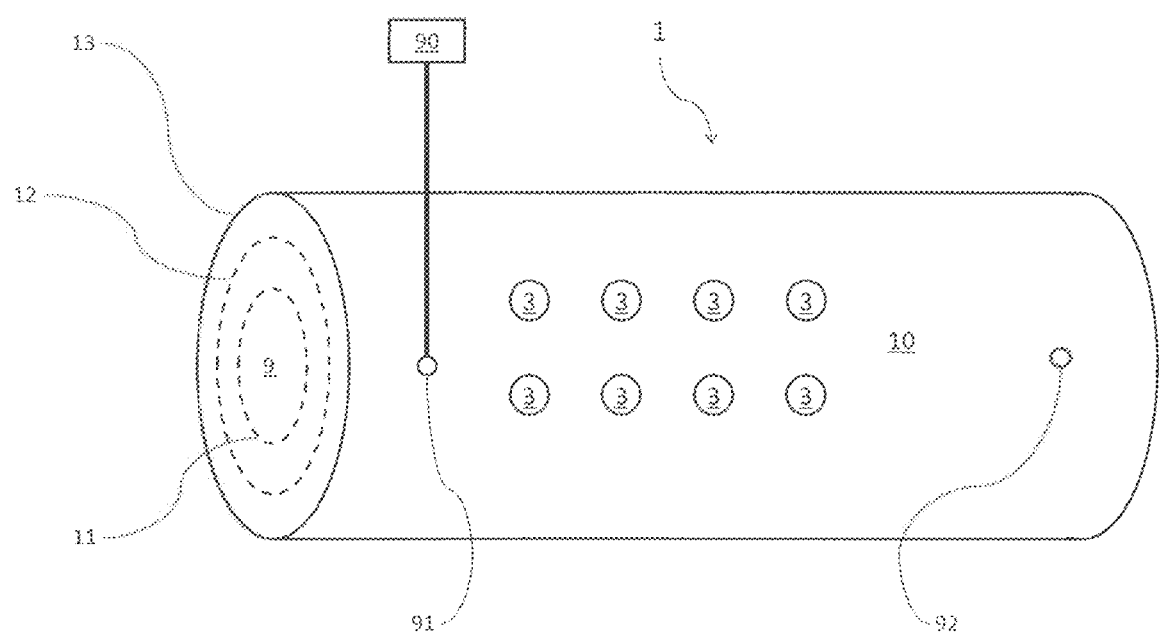
FIG. 4 shows an embodiment of a UV lamp according to an embodiment of the invention.

As shown in FIGS. 1 and 4, the UV lamp 1 further comprises an axial hollow interior 9, an inlet opening 91 and an outlet opening 92 in the outer surface 10 adapted to allow fluid communication from the inlet opening 91 to the outlet opening 92 via the hollow interior 9, and a flushing arrangement 90 adapted to provide a fluid to the inlet opening 91. The axial conductors 12, 13 and the electrically insulating material 11 are arranged concentrically to have a cylindrical shape, which provides the UV lamp 1 with the axial hollow interior 9. The first axial conductor 12 being continuous the inner surface 12 provides the UV lamp 1 with a liquid tight tube sealing the interior of the UV lamp 1 from liquid being flushed through the axial hollow interior 9. The UV lamp 1 having a plurality of LEDs is illustrated in FIG. 4.

Figure 2:
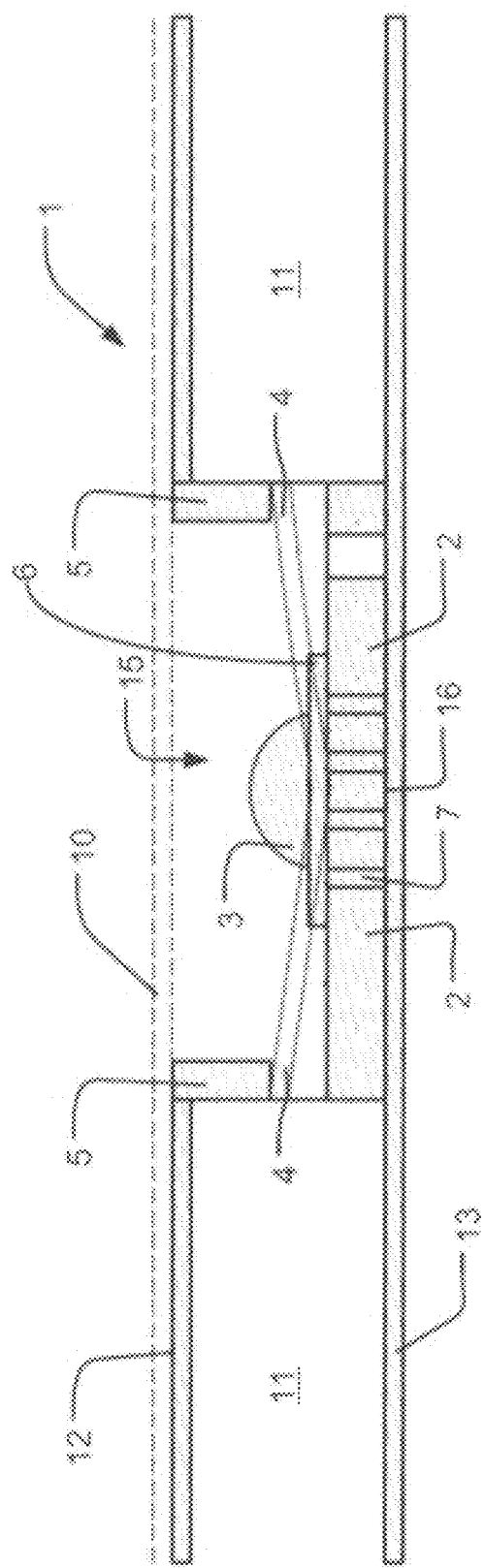
FIG. 2 shows a cross-sectional view of a LED mounted in recess in a UV lamp according to the invention.
Figure 3:
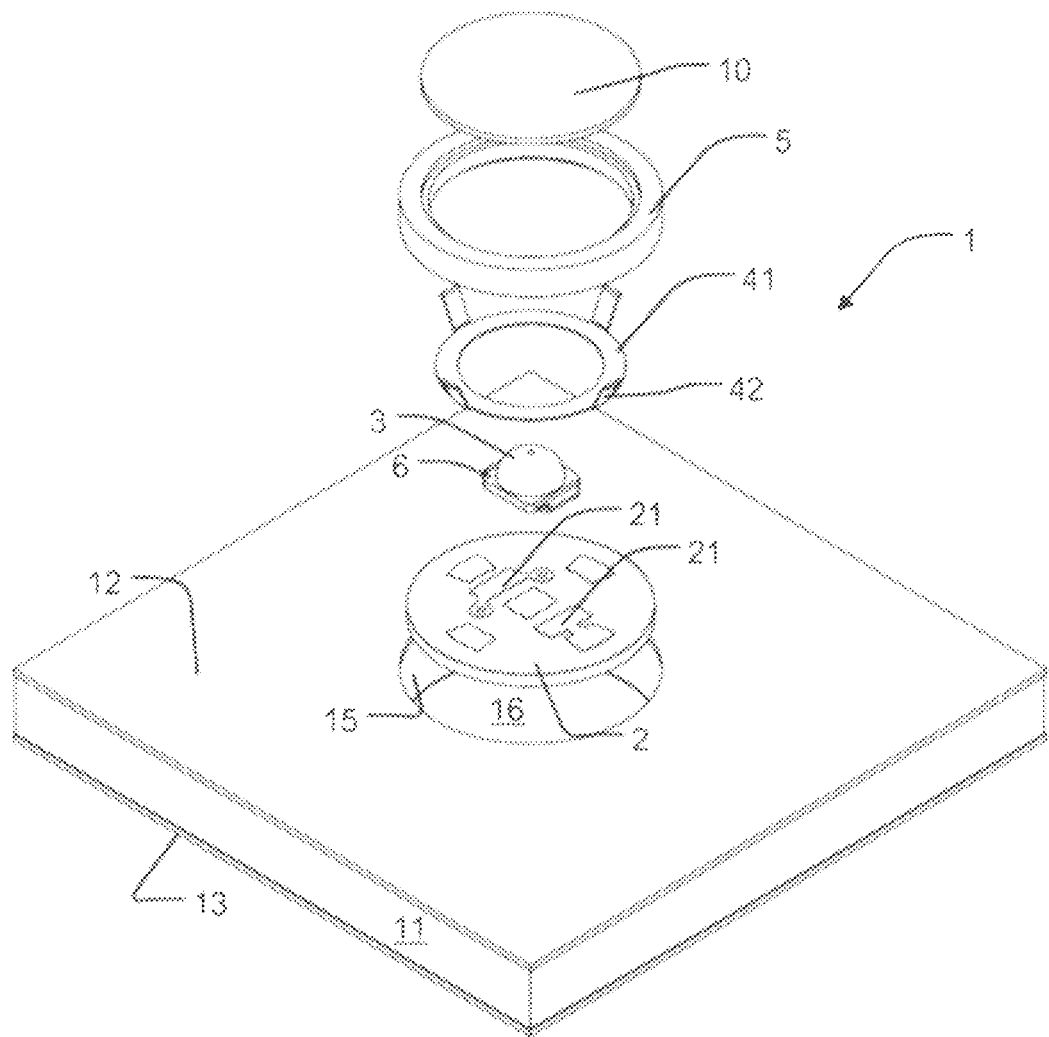
FIG. 3 shows an exploded view of a LED mounted in recess in a UV lamp according to the invention.

FIG. 2 shows a cross-section of a part of UV lamp 1 of the invention and FIG. 3 shows an exploded view of the part depicted in FIG. 2. It is to be understood that while FIG. 2 and FIG. 3 indicate a planar design of the UV lamp 1, it is preferred that the UV lamp 1 has a circular cross-section as shown in FIG. 1, and all features described below can be amended to comply with a round cross-section of the UV lamp 1. Specifically, the cross-section shown in FIG. 2 is part of the UV lamp 1 where the first axial conductor, the electrically insulating material and the second axial conductor are arranged in layers. In the following, the structure comprising the first axial conductor, the electrically insulating material and the second axial conductor will be referred to as the "layers".

The layers in this embodiment comprise an electrically insulating material 11 in the form of an electrically insulating layer, e.g. polyethylene, positioned between two electrically conducting layers 12,13. The electrically conducting anode layer 12 is shown as an "electrically conducting front layer", and cathode layer 13 is shown as an "electrically conducting back layer". It is also possible that the front layer is the cathode layer and that the back layer is the anode layer. The electrically conducting layers 12,13 are made of e.g. aluminium, but may be made electrically conducting by the use of other conducting materials. When aluminium is used it is preferably anodised, e.g. to have an oxide layer of about 20 μm thickness. The layers are provided with a recess 15, in this case a cylindrical recess, through the electrically conducting layer 12 and the electrically insulating material 11. The recess 15 comprises a bottom 16 constituted by the electrically conducting back layer 13 and wall(s) constituted by the electrically insulating material 11 and the electrically conducting layer 12. The recess 15 may also have perimeters of other shapes, e.g. superficial shapes, such as square, rectangular, triangular perimeters etc. Inside the hole a circuit board 2, e.g. a printed circuit board (PCB), is provided. The circuit board 2 has the same shape and size, or slightly smaller size, than the bottom of the recess 15. It may also be even smaller, larger or a different shape. A surface mounted device (SMD) UV LED 3 is attached to the circuit board 2. Alternatively, another kind of LED can also be used. The SMD UV LED 3 comprises a first and a second electrical terminal (not shown), functioning as the cathode and anode, respectively.

In the embodiment shown, the first electrical terminal is in a first electrical connection with the electrically conducting front layer 12, and the second electrical terminal is in second electrical connection with the electrically conducting back layer 13.

The first electrical connection between the electrically conducting front layer 12 and the first electrical terminal is formed via a conductor, preferably a printed conductor, on the circuit board 2 and further conductors as appropriate. In the embodiment shown, the first electrical terminal is in electrical connection with an electrically conducting element 4, e.g. a resilient electrically conducting element in the form of a wave spring, a washer ring, a spring washer, a disc spring or a coil etc., positioned along the circumference of the recess 15, which is further in electrical connection with an electrically conducting retaining element 5, extending along the circumference of the hole and between the electrically conducting front layer 12 and the electrically conducting element 4. The conducting retaining element 5 is especially appropriate when the recess 15 is made into preformed layers, e.g. a dibond plate. When the hole is established in one or both layers, in particular the "front layer", of a layers before assembly of the layers a conducting retainer element is typically not used. In a specific embodiment the electrically conducting element 41 is a metallic ring with one or more legs, e.g. 4 legs, providing resilience. The electrically conducting retaining element 5 may be a metal ring, e.g. a copper or aluminium ring, at the circumference of the circuit board 2. The electrically conducting element 4 is preferably made of a suitable metal e.g. spring metal, copper, an aluminium alloy etc. The electrically conducting element 4 is in press between the circuit board 2 and an electrically conducting retaining element 5 in the form of an, e.g. metallic, electrically conducting retainer ring, extending along the circumference of the hole and between the electrically conducting front layer 12 and the electrically conducting element 4. The electrically conducting element 4, e.g. in the form of a wave spring, is waved along the edge such that the edge of the wave spring alternately is in contact with the electrically conducting retaining element 5 and the circuit board 2. The electrically conducting retaining element 5 thus establishes an electrical contact to the electrically conducting front layer 12. The electrically conducting element 4 and the electrically conducting retainer ring 5 further keep the circuit board 2 in place. The circuit board 2, the electrically conducting element 4, and the electrically conducting retaining element 5 can be considered to constitute an adapter for mounting in the recess 15. In a specific embodiment the circuit board 2, the electrically conducting element 4, and the electrically conducting retaining element 5 are joined together for easy insertion of the adapter in the whole. In another embodiment the circuit board 2, and optionally the electrically conducting element 4, and the electrically conducting retaining element 5 are contained in a holder or the like, which holder can be inserted into the hole.

Alternatively, the electrically conducting element 4 may be dispensed with such that the electrically conducting retaining element 5 is in direct contact with the supply circuit on the circuit board 2. As a further alternative the electrically conducting front layer 12 may extend over the electrically conducting retaining element 5 such that the electrically conducting front layer 12 keeps the electrically conducting retaining element 5 in place, for example when the electrically conducting front layer 12 has been prepared by extrusion for subsequent assembly into the layers.

The second electrical connection to the electrically conducting rear layer 13 is formed from the second electrical terminal via a conductor, preferably printed, on the circuit board 2 extending to a conductor mounted on, in or through the circuit board 2. In the embodiment shown, the conductor extends through a hole in the circuit board 2 to the electrically conducting rear layer 13. The conductor may take the form of an electrically conducting pipe, a cable or a rod, etc.

The adapter is furthermore provided with a thermal conductor component 6, e.g. of silicon carbide, on which the LED 3 is mounted, further comprising thermal conductors 7, in the form of copper threads, extending between the thermal conductor component 6 and the electrically conducting back layer 13 through the circuit board 2. Other heat conducting materials may be used as well.

Additionally, as all the components/elements in the recess may be flush with the surface of the electrically conducting front layer 12, i.e. there are no protruding parts extending beyond the surface of the electrically conducting front layer 12, an additional layer in the form of quartz glass layer 10 is provided on top of the electrically conducting front layer 12. The quartz glass layer 10 may only cover the hole, for example if it is in the form of a recessed lens, or it may also be dispensed with. The quartz glass layer may be used for protecting the electronic component from water, e.g. together with a seal (not shown), and/or scatter and/or diffuse and/or focus UV light emitted from the UV LED.

Further attachment means may be used to keep the adapter in place, such as an adhesive or paste that may be electrically conducting. Also, an optical lens may be attached as the quartz glass layer 10 or be incorporated therein.

In the embodiment depicted in FIG. 3, the electrically conducting element has a base 41 and is provided with four conducting resilient legs 42 extending between the base 41 and an electrically conducting retaining element 5. Alternatively, the electrically conducting element 41 may be provided with an arbitrary number of legs such as three to six legs. FIG. 3 also shows a printed circuit 21 on the circuit board, e.g. in the form of an aluminium plate with a printed circuit. The aluminium secures a good thermal contact to the UV LED's thermal conductor component 6. The circuit board 2 is coated on the back side with a thin layer of gold to provide a good thermal and electrical contact to the bottom of the recess in the form of the electrically conducting rear layer 13. The gold coating may be dispensed with. The UV lamp may also comprise, e.g. between the circuit board 2 and the electrically conducting back layer 13, a thermal paste to provide better thermal contact to thereby leading heat away from the LED and further to prevent corrosion of the electrically conducting back layer 13, e.g. when the electrically conducting back layer 13 is made from aluminium. When the UV lamp comprises a thermal paste it may also comprise a thin toothed washer between the circuit board 2 and the electrically conducting back layer 13 in order to avoid electrical resistance from the thermal paste.

Although some embodiments have been described and shown in detail, the invention is not restricted to them, but may also be embodied in other ways within the scope of the subject matter defined in the following claims. In particular, it is to be understood that other embodiments may be utilized, and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

It should be emphasised that the term "comprises/comprising" when used in this specification is taken to specify the presence of stated features, integers, steps or components but does not preclude the presence or addition of one or more other features, integers, steps, components or groups thereof.

In a specific embodiment, the UV lamp 1 has an axial hollow interior 9 and a flushing arrangement 90 adapted to provide a flow of water to the inlet opening 91 so that water flowing through the UV lamp 1 can be disinfected or sterilized. The UV lamp 1 thus has a cylindrical shape with an inner diameter of 10 cm and a length of 1 m, and in use the UV lamp 1 can be mounted downstream of a filter for removing coarse particles in the water. In this embodiment the inner surface 12 is reflective and contains 1 UV LED 3 per $cm^2$, which can provide a UV light intensity of about 1 $mW/cm^2$, This embodiment can appropriately sterilize water flowing through the UV lamp 1 at about 5 cm/s, or 1.5 $m^3/h$.

What is claimed is:
1. A UV lamp having an axial dimension normal to a cross-section having a cross-sectional area with a ratio of the axial dimension to the cross-sectional area configured such that the UV lamp has a longitudinal shape, the UV lamp comprising:
   a first axial conductor separated from a second axial conductor by an electrically insulating material, at least one of the first axial conductor and the second axial conductor defining an outer surface; and a light emitting diode (LED) capable of providing light at a wave-length in the range of 100 nm to 400 nm, the LED having a first electrical terminal electrically connected to the first axial conductor and a second electrical terminal connected to the second axial conductor, wherein the LED is mounted to emit light from the outer surface.

2. The UV lamp according to claim 1, further comprising an axial hollow interior, an inlet opening and an outlet opening in the outer surface adapted to allow fluid communication from the inlet opening to the outlet opening via the hollow interior, and a flushing arrangement adapted to pro-vide a fluid to the inlet opening.

3. The UV lamp according to claim 1, wherein the first axial conductor forms the outer surface, said first axial conductor being continuous along a perimeter of the cross-section at a fraction of the axial dimension in the range of 10% to 100%.

4. The UV lamp according to claim 1 further comprising a window transparent to light at a wavelength in the range of 100 nm to 400 nm, the window adapted to provide a water tight cover for the LED and let light emit-ted from the LED through.

5. The UV lamp according to claim 1, wherein the window is arranged as or is integrated in a housing for the UV lamp.

6. The UV lamp according to claim 1 comprising a plurality of LEDs arranged so that light is emitted at a fraction in the range of 50% to 100% of a perimeter of the cross-section.

7. The UV lamp according to claim 1 further comprising a power supply capable of providing a direct current between the first axial conductor and the second axial conductor, the power supply further being capable of providing a first constant voltage equal to or higher than a nominal forward voltage (Vf) of the LED and a second constant voltage below the nominal forward voltage (Vf) of the LED.

8. The UV lamp according to claim 7 further comprising an electronic component being operable at the second constant voltage.

9. A UV lamp having an axial dimension normal to a cross-section having a cross-sectional area with a ratio of the axial dimension to the cross-sectional area configured such that the UV lamp has a longitudinal shape, the UV lamp comprising:

a first axial conductor separated from a second axial conductor by an electrically insulating material, at least one of the first axial conductor and the second axial conductor defining an inner surface;

an axial hollow interior, an inlet opening and an outlet opening in the outer surface adapted to allow fluid communication from the inlet opening to the outlet opening via the hollow interior, and a flushing arrangement adapted to provide a fluid to the inlet opening; and a light emitting diode (LED) capable of providing light at a wave-length in the range of 100 nm to 400 nm, the LED having a first electrical terminal electrically connected to the first axial conductor and a second electrical terminal connected to the second axial conductor, wherein the LED is mounted to emit light from the inner surface to-wards the axial hollow interior.

10. The UV lamp according to claim 9, wherein the inner surface contains at least 1 LED/cm2.

11. The UV lamp according to claim 9, wherein the inner surface is capable of providing light at a wavelength in the range of 100 nm to 400 nm of at least 1 mW/cm2.

12. A method of disinfecting a surface comprising the steps of:

providing a UV lamp having an axial dimension normal to a cross-section having a cross-sectional area with a ratio of the axial dimension to the cross-sectional area configured such that the UV lamp has a longitudinal shape, the UV lamp comprising a first axial conductor separated from a second axial conductor by an electrically insulating material, at least one of the first axial conductor and the second axial conductor defining an outer sur-face; a light emitting diode (LED) capable of providing light at a wavelength in the range of 100 nm to 400 nm, the LED having a first electrical terminal electrically connected to the first axial conductor and a second electrical terminal connected to the second axial conductor; wherein the LED is mounted to emit light from the outer surface, and irradiating the surface at a UV dose of at least 2 mJ/cm2.

13. A method of disinfecting a surface comprising the steps of:

providing a UV lamp having an axial dimension normal to a cross-section having a cross-sectional area with a ratio of the axial dimension to the cross-sectional area configured such that the UV lamp has a longitudinal shape, the UV lamp comprising: a first axial conductor separated from a second axial conductor by an electrically insulating material, at least one of the first axial conductor and the second axial conductor defining an outer sur-face; a light emitting diode (LED) capable of providing light at a wavelength in the range of 100 nm to 400 nm, the LED having a first electrical terminal electrically connected to the first axial conductor and a second electrical terminal connected to the second axial conductor; wherein the LED is mounted to emit light from the outer surface, which UV lamp further comprises an axial hollow interior, an inlet opening and an outlet opening in the outer surface adapted to allow fluid communication from the inlet opening to the outlet opening via the hollow interior, and a flushing arrangement adapted to pro-vide a fluid to the inlet opening, irradiating the surface at a UV dose of at least 2 mJ/cm2, and flushing the surface by applying at least 0.2 mL/cm2/s of a liquid to the surface from the flushing arrangement.

* * * * *